(12) United States Patent
Yu et al.

(10) Patent No.: US 11,988,580 B2
(45) Date of Patent: May 21, 2024

(54) METHOD FOR MONITORING FORESTRY MICROENVIRONMENT

(71) Applicant: Shandong Normal University, Ji'nan (CN)

(72) Inventors: Guanliu Yu, Ji'nan (CN); Yu Zhang, Ji'nan (CN)

(73) Assignee: SHANDONG NORMAL UNIVERSITY, Jinan (CN)

( * ) Notice: Subject to any disclaimer, the term of this patent is extended or adjusted under 35 U.S.C. 154(b) by 0 days.

(21) Appl. No.: 18/378,014

(22) Filed: Oct. 9, 2023

(65) Prior Publication Data
US 2024/0085279 A1    Mar. 14, 2024

(30) Foreign Application Priority Data

Nov. 2, 2022  (CN) .......................... 202211364044.3

(51) Int. Cl.
*G01N 1/08*    (2006.01)
*G01N 33/24*   (2006.01)

(52) U.S. Cl.
CPC .............. *G01N 1/08* (2013.01); *G01N 33/24* (2013.01)

(58) Field of Classification Search
CPC .................................. G01N 1/08; G01N 33/24
See application file for complete search history.

(56) References Cited

U.S. PATENT DOCUMENTS

2023/0304901 A1*  9/2023  Peng .................... G01N 1/08

FOREIGN PATENT DOCUMENTS

| CN | 110361222 A | * | 10/2019 | ............. G01N 1/08 |
| CN | 211452908 U |   | 9/2020  |                        |
| CN | 114354247 A |   | 4/2022  |                        |
| CN | 217237244 U |   | 8/2022  |                        |
| CN | 116358929 A | * | 6/2023  |                        |
| CN | 116698498 B | * | 10/2023 |                        |

OTHER PUBLICATIONS

CNIPA, Notification of First Office Action for Chinese application CN202211364044.3, Apr. 12, 2023.
CNIPA, Notification to grant patent right for Chinese application CN202211364044.3, Apr. 26, 2023.

* cited by examiner

*Primary Examiner* — John Fitzgerald
(74) *Attorney, Agent, or Firm* — Zhigang Ma

(57) ABSTRACT

The present invention relates to the technical field of environmental monitoring, and particularly relates to a method for monitoring a forestry microenvironment, comprising the following steps: S1: moving a forestry detection vehicle to a monitoring position; S2: inserting the sampling device on the forestry detection vehicle into the soil at a corresponding depth; S3: disconnecting the sampled soil, and withdrawing the sampling device from the forestry detection vehicle to complete the sampling process; S4: weighing the above soil sample quantitatively, and detecting the soil standard solution through a detection instrument. The sampling device in S1 comprises a rack; an outer sleeve is arranged in the rack; and a sampling mechanism is arranged in the outer sleeve.

9 Claims, 8 Drawing Sheets

METHOD FOR MONITORING FORESTRY MICROENVIRONMENT

TECHNICAL FIELD

The present invention relates to the technical field of forestry, and particularly relates to a method for monitoring a forestry microenvironment.

BACKGROUND

A device for monitoring a microenvironment of state-owned forest farms with application number CN202120596858.4 specifically discloses a box body provided with a monitoring assembly. The top of the box body is provided with a solar panel connected with a battery in the box body. The top of the box body on one side of the solar panel is provided with a driving assembly for driving the solar panel to rotate, which greatly extends the effective service life of the driving assembly. A protective cover is detachably connected with the top of the box body by screws. The installation is simple, the disassembly is convenient, and the time and cost of maintenance are reduced. Because the existing device for monitoring the forestry microenvironment needs to monitor the microenvironment of forestry soil and to sample the forestry soil in the monitoring process, the existing device for monitoring the forestry microenvironment drills a sampler into a soil layer for sampling, and can only drill a certain fixed depth of soil in one sampling process. Considering the objectivity and the accuracy of the monitoring results, it is necessary to take multiple samples to drill the soil at different depths of soil layers. Thus, the sampling efficiency of the existing soil sampling device is low, and great burden is brought to the forestry microenvironment monitoring. Therefore, a method for monitoring a forestry microenvironment is proposed.

SUMMARY

The purpose of the present invention is to provide a method for monitoring a forestry microenvironment in order to solve the defect in the prior art that the device for monitoring the forest microenvironment drills a sampler into a soil layer for sampling, and can only drill a certain fixed depth of soil in one sampling process, the sampling efficiency of the soil is low, and great burden is brought to the forestry microenvironment monitoring.

To achieve the above purpose, the present invention adopts the following technical solution:

A method for monitoring a forestry microenvironment is designed, which comprises the following steps:

S1: moving a forestry detection vehicle to a monitoring position, starting a sampling device installed on the forestry detection vehicle, and drilling a sampling end into soil by the sampling device;

S2: inserting the sampling device on the forestry detection vehicle into the soil at a corresponding depth;

S3: disconnecting the sampled soil, and withdrawing the sampling device from the forestry detection vehicle to complete the sampling process;

S4: weighing the above soil sample quantitatively, placing the soil sample in a conical detection bottle, adding a quantitative solvent to the conical detection bottle, dissolving and filtering to obtain a standard solution for soil detection, and detecting the soil standard solution through a detection instrument.

The sampling device in S1 comprises a rack; the rack is arranged as a portal frame; an outer sleeve is arranged in the rack; the upper end of the outer sleeve is rotatably installed on the rack; the inner end in the outer sleeve is provided with an inner disc; the inner disc is rotatably installed at the inner side of the outer sleeve; the inner disc is fixedly provided with a connecting frame; the end of the connecting frame is fixedly connected to the rack; a sampling mechanism is arranged in the outer sleeve; and the lower end of the sampling mechanism extends outside the outer sleeve and is connected with the inner disc.

Preferably, the sampling mechanism further comprises an inner cylinder; the upper end of the inner cylinder extends into the outer sleeve; the inner cylinder is provided with a plurality of upper and lower equidistant perforations; the perforations penetrate through the inner cylinder and the plurality of perforations located at the same height are distributed in a circular array; storage grooves are arranged at bottoms in the perforations; the bottom of the inner cylinder is fixedly provided with a drill bit; the inner side of the outer sleeve is provided with a plurality of spline grooves distributed in a circular array; the outer side of the inner cylinder is fixedly provided with a plurality of splines distributed in a circular array; the splines are matched with splines of the spline grooves; the upper end in the inner cylinder is rotatably provided with a connecting piece; the sampling mechanism further comprises a screw rod; the screw rod is arranged in the inner cylinder; the upper end of the screw rod is rotatably installed at the bottom of the inner disc; the lower end of the screw rod penetrates through the connecting piece and is in threaded connection with the connecting piece; the top of the inner disc is rotatably provided with a connecting shaft; the connecting shaft penetrates through the inner disc and is fixedly connected with the screw rod; the top of the outer sleeve is fixedly provided with a connecting ring; the connecting ring is sleeved and fixedly provided with a tooth ring; sealing plugs are arranged in the storage grooves; the sealing plugs are in interfere fit with the storage grooves; the sampling mechanism further comprises a plurality of connecting ropes; the connecting ropes penetrate through the inner cylinder and the storage grooves and are fixedly connected with a plurality of sealing plugs in the same column; the upper ends of the connecting ropes are fixedly connected to the bottom of the inner disc; the sampling mechanism further comprises a driving assembly; and the driving assembly is installed on the rack and connected with the connecting shaft.

Preferably, the bottom of the screw rod is fixedly provided with a stopper, and the surface of the screw rod is sprayed with an anti-rust coating.

Preferably, the method further comprises scale lines arranged at the outer side of the inner cylinder.

Preferably, both ends of the bottom of the rack are fixedly provided with embedded parts; the tops of the embedded parts are provided with installing grooves; the installing grooves are arranged in U shape; both ends of the embedded parts are provided with guide ports; the guide ports penetrate through the embedded parts and are communicated with the installing grooves; and the bottoms of the embedded parts are arranged in a triangular cone.

Preferably, two symmetrically distributed limiting parts are arranged in the installing grooves; one end of the limiting parts is sharpened; one end of the limiting parts can penetrate through the guide ports; the upper sides of the limiting parts are provided with guide plates; the guide plates are located in the installing grooves and fixedly connected to the embedded parts; the sampling mechanism further comprises a linkage mechanism; and the linkage mechanism is installed on the rack and connected with a plurality of limiting parts.

Preferably, the linkage mechanism comprises two groups of linkage assemblies in mirror distribution; the linkage assemblies comprise two spaced transverse shafts; the transverse shafts are rotatably installed in the installing grooves respectively; the transverse shafts are fixedly provided with two spaced friction wheels; the limiting parts are fixedly provided with two spaced friction strips; the friction strips are in transmission with the friction wheels by friction force; worm wheels are fixedly installed on the two transverse shafts; the tops of the embedded parts are fixedly provided with two spaced supporting seats; two symmetrically distributed worms are rotatably installed between the two supporting seats; the opposite ends of the two worms are fixedly connected; and the worms are engaged with the worm wheels on the same side.

Preferably, the driving assembly comprises a motor; the motor is fixedly connected to the rack; the output shaft end of the motor is fixedly provided with a first rotating shaft; the end of the first rotating shaft is fixedly provided with a first bevel gear; the rack is rotatably provided with a second rotating shaft; the lower end of the second rotating shaft is fixedly provided with a second bevel gear; the second bevel gear is engaged with the first bevel gear; a gear is fixedly installed on the second rotating shaft; the gear is engaged with the tooth ring; and the upper end of the second rotating shaft and the upper end of the connecting shaft are provided with a first belt mechanism.

Preferably, both ends of the top of the rack are fixedly provided with grips, the grips are sleeved with non-slip rubber sleeves, and the corners of the rack are rounded.

Preferably, the method further comprises a second belt mechanism and a third belt mechanism; one end of the second belt mechanism and one end of the third belt mechanism are installed on the first rotating shaft; and the other end of the second belt mechanism and the other end of the third belt mechanism are installed on the worms on both sides respectively.

The method for monitoring the forestry microenvironment proposed in the present invention has the following beneficial effects: the driving assembly drives the connecting shaft to rotate, and also drives the tooth ring to rotate; the connecting shaft rotates synchronously with the screw rod; and the screw rod rotates and drives the inner cylinder to move downward in a vertical direction. The tooth ring, the connecting ring and the outer sleeve rotate synchronously, and the outer sleeve makes the inner cylinder rotate synchronously through the transmission action of the spline grooves and the splines, so that the drill bit at the lower end of the inner cylinder drills downward. The inner cylinder moves into the soil layer, and the inner cylinder stops after moving to a certain fixed depth. At this time, the connecting ropes are in a stretched state and the connecting ropes pull a plurality of sealing plugs. By driving the sealing plugs away from the upper ports of the storage grooves, the storage grooves are in an open state. At this time, the soil at different depths can enter the storage grooves of different heights respectively, and then the inner cylinder is taken out. Thus, the device can take out soil samples at different depths through single sampling, which can effectively improve the sampling efficiency and alleviate the labor burden of the monitoring work of the forestry microenvironment.

The first rotating shaft rotates and drives the worms at both ends to rotate through the second belt mechanism and the third belt mechanism. The worms rotate and drive the worm wheels to rotate. Because the rotating directions of the two connected worms are opposite, the worm wheels at both ends have opposite rotating directions. The worm wheels rotate synchronously with the transverse shafts; the friction wheels on the transverse shafts rotate and drive the friction strips to move; the friction strips move synchronously with the limiting parts; and the limiting parts at both sides are inserted into the soil layer synchronously. The device is fixed by inserting the limiting parts into the soil layer, which can further improve the stability of the device during operation. Compared with the existing manual fixing mode, the present invention saves the physical strength of the personnel and fixes the device more firmly. At the same time, the personnel are not in direct contact with the device, thereby avoiding the discomfort of the personnel.

Figure 1:
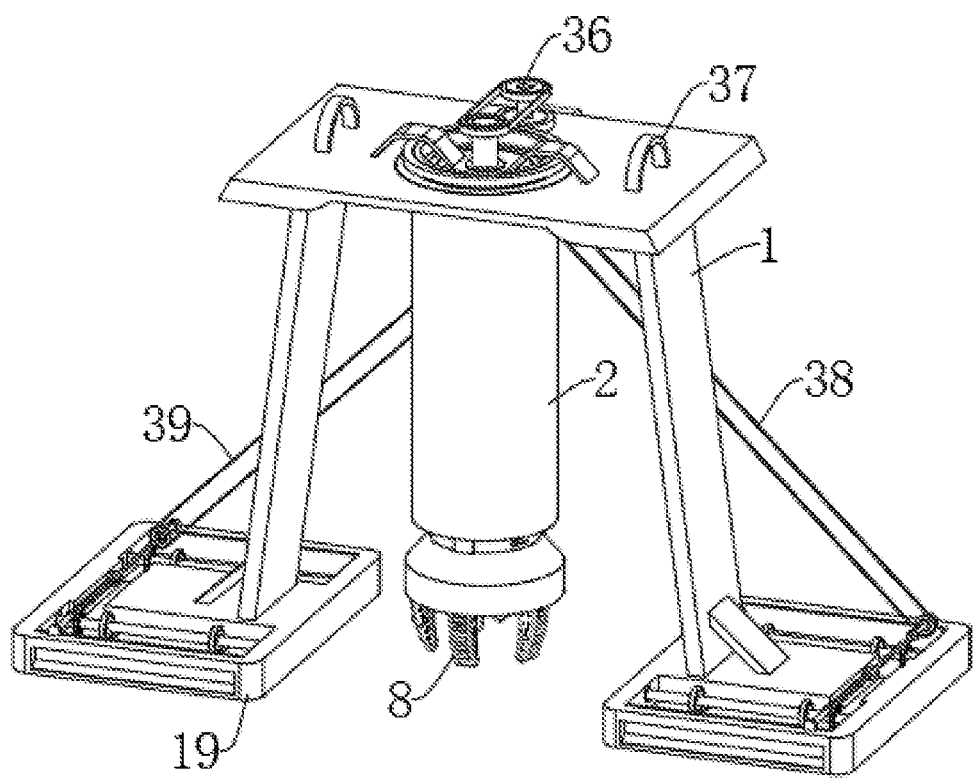
FIG. 1 is a structural schematic diagram 1 of a sampling device of a method for monitoring a forestry microenvironment proposed in the present invention.

In the figures: rack 1, outer sleeve 2, inner disc 3, connecting frame 4, inner cylinder 5, perforation 6, storage groove 7, drill bit 8, spline groove 9, spline 10, connecting piece 11, screw rod 12, stopper 13, connecting shaft 14, connecting ring 15, tooth ring 16, sealing plug 17, connecting rope 18, embedded part 19, installing groove 20, guide port 21, limiting part 22, guide plate 23, transverse shaft 24, friction wheel 25, friction strip 26, worm wheel 27, supporting seat 28, worm 29, motor 30, first rotating shaft 31, first bevel gear 32, second rotating shaft 33, second bevel gear 34, gear 35, first belt mechanism 36, grip 37, second belt mechanism 38, and third belt mechanism 39.

DETAILED DESCRIPTION

The technical solutions in the embodiments of the present invention will be clearly and fully described below in combination with the drawings in the embodiments of the present invention.

Embodiment 1

Figure 2:
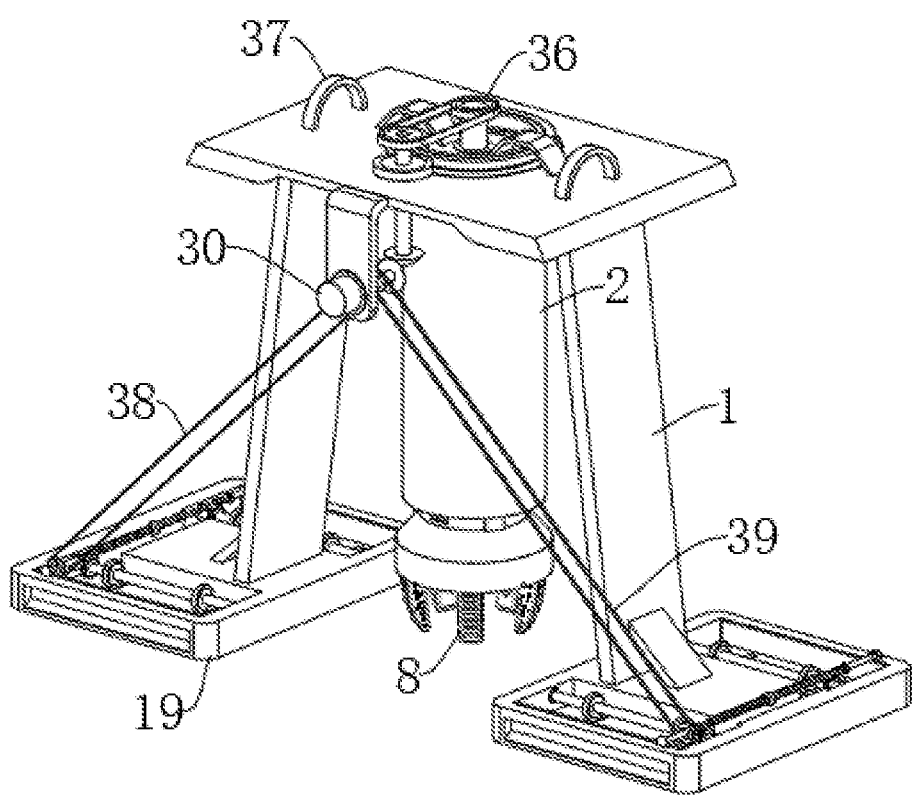
FIG. 2 is a structural schematic diagram 2 of a sampling device of a method for monitoring a forestry microenvironment proposed in the present invention.
Figure 3:
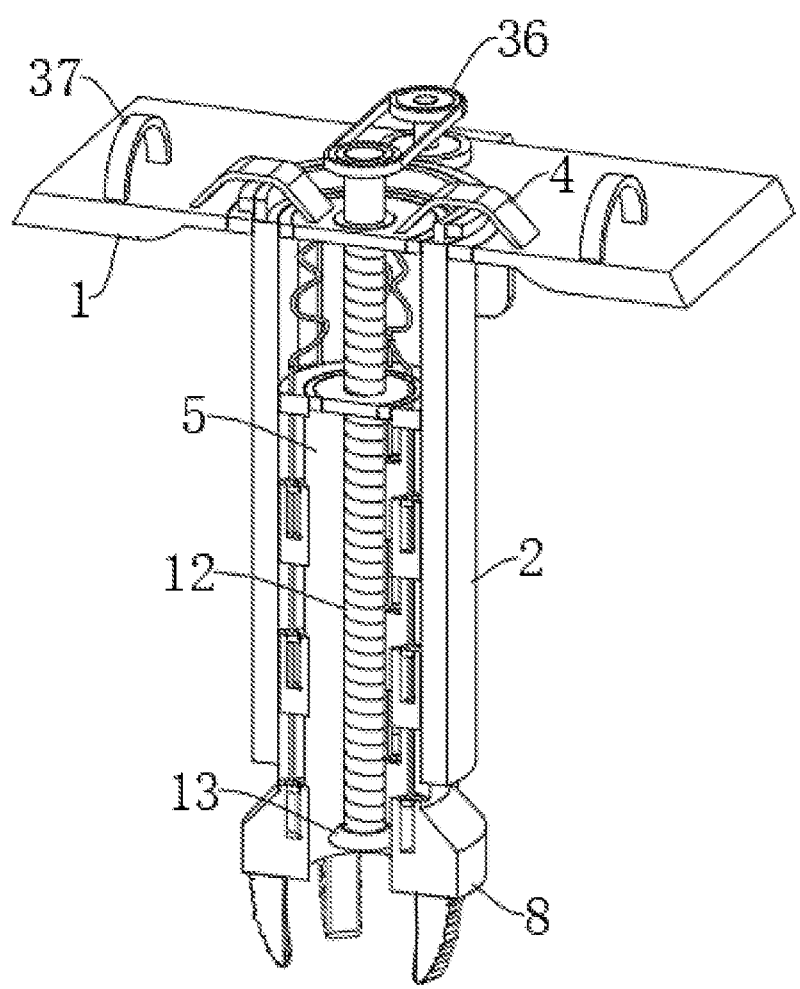
FIG. 3 is a partial structural amplified sectional view of a sampling device of a method for monitoring a forestry microenvironment proposed in the present invention.
Figure 4:
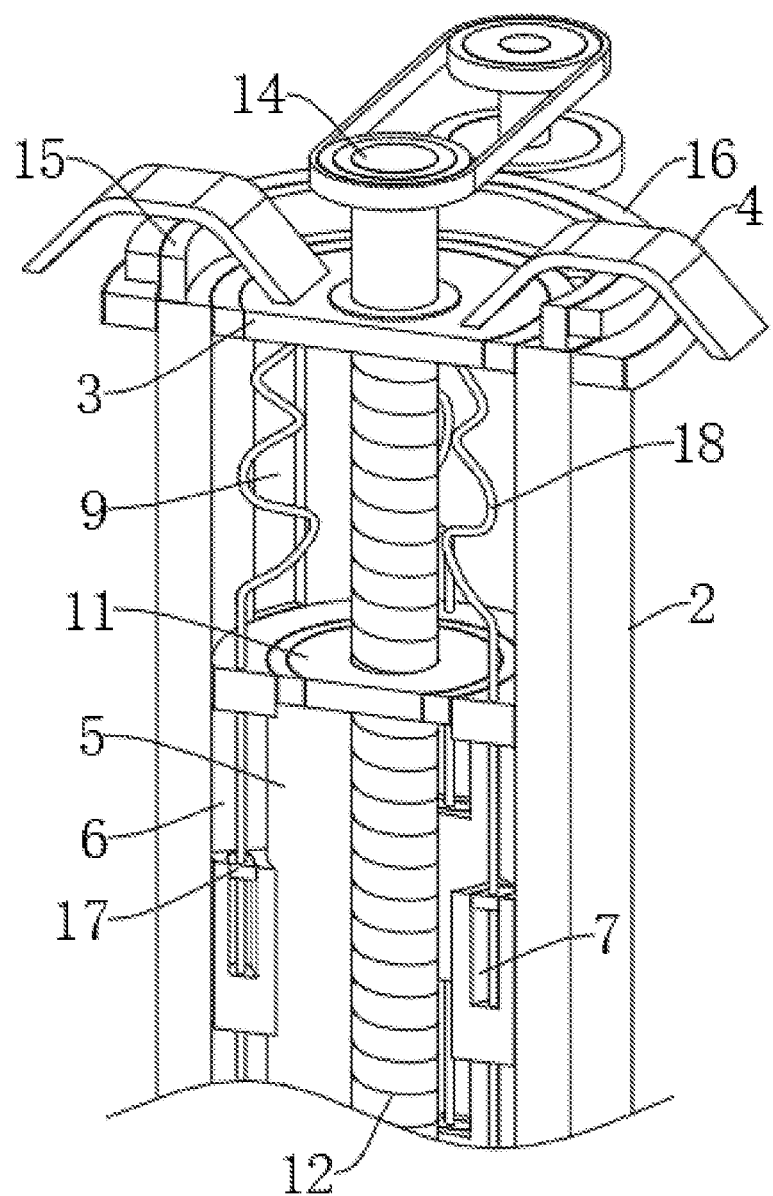
FIG. 4 is a partial structural amplified sectional view at an outer sleeve of a sampling device of a method for monitoring a forestry microenvironment proposed in the present invention.
Figure 5:
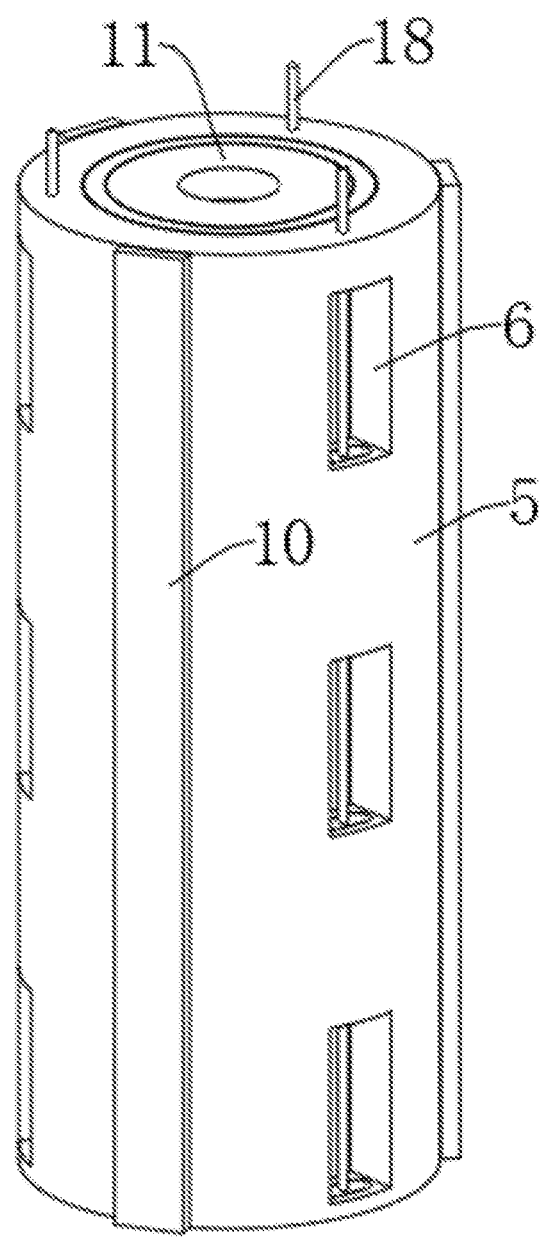
FIG. 5 is an amplified schematic diagram of an inner cylinder of a sampling device of a method for monitoring a forestry microenvironment proposed in the present invention.
Figure 6:
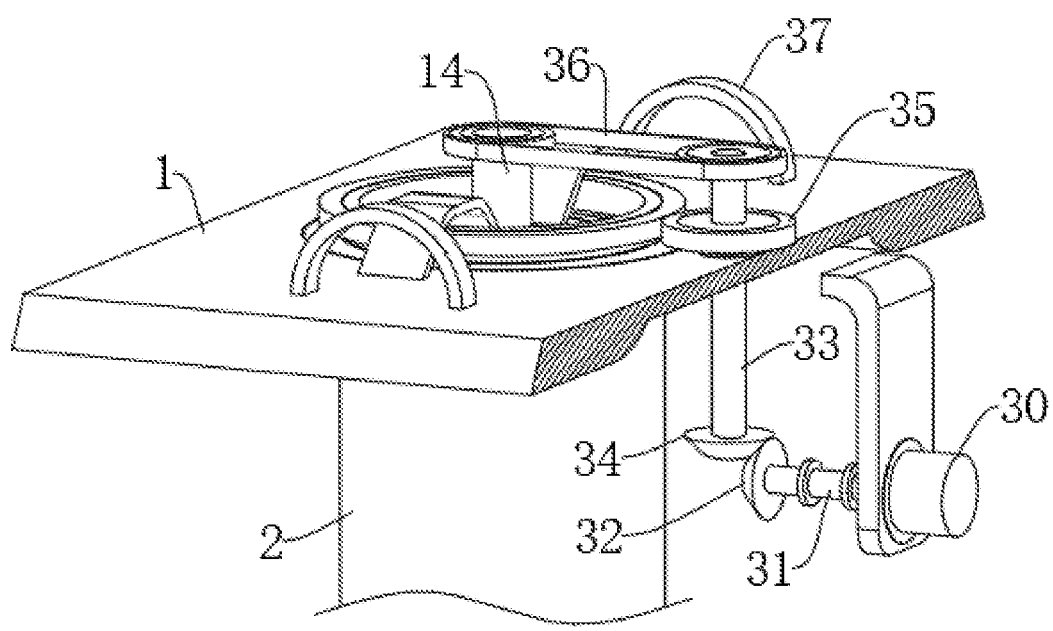
FIG. 6 is a partial structural amplified sectional view at a motor of a sampling device of a method for monitoring a forestry microenvironment proposed in the present invention.
Figure 7:
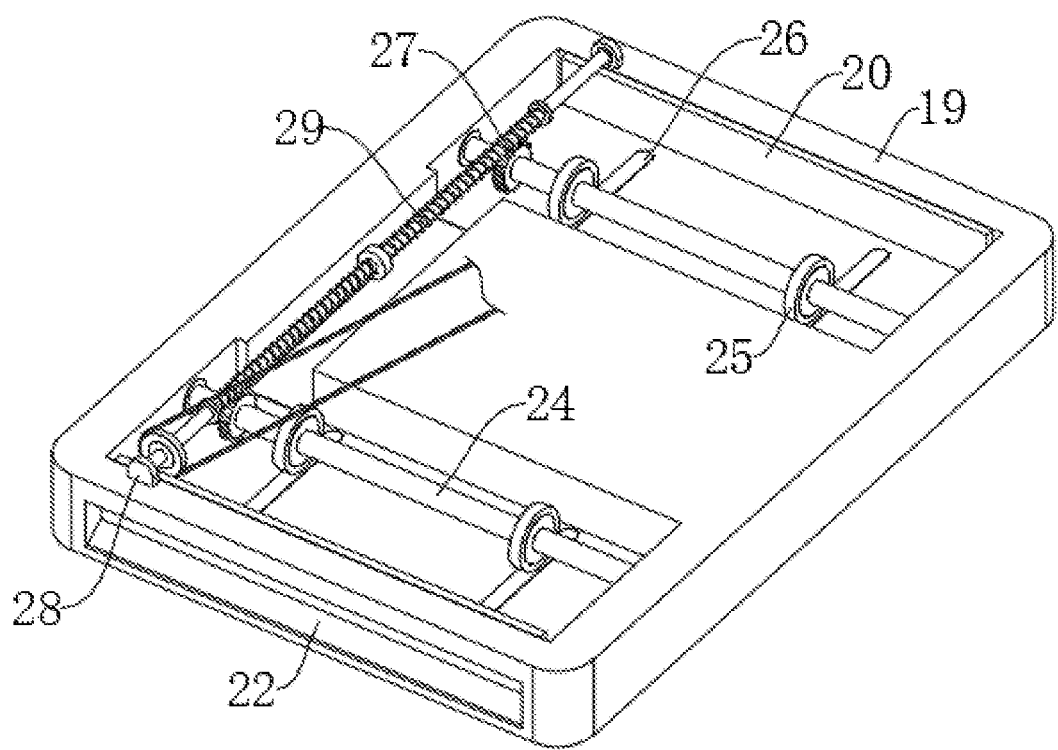
FIG. 7 is a partial structural amplified schematic diagram at an embedded part of a sampling device of a method for monitoring a forestry microenvironment proposed in the present invention.
Figure 8:
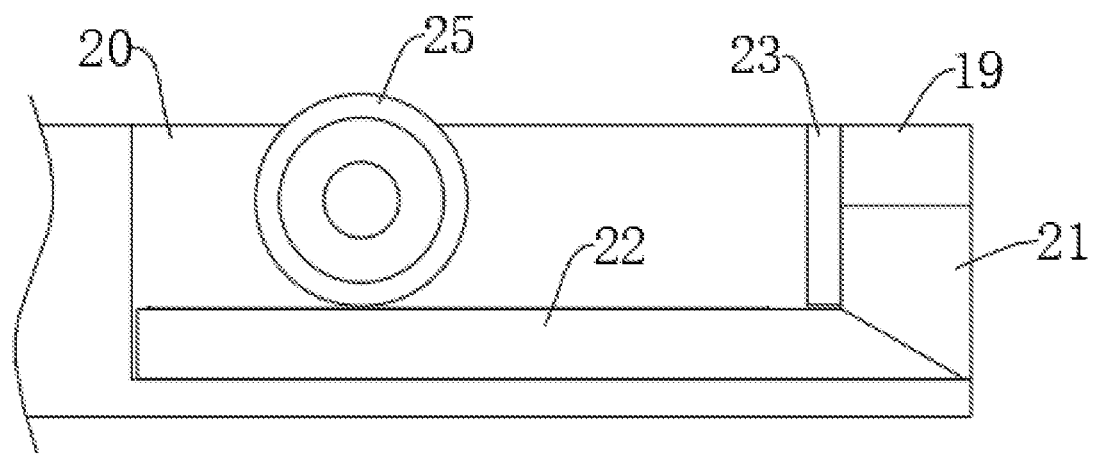
FIG. 8 is a partial structural amplified sectional view at an embedded part of a sampling device of a method for monitoring a forestry microenvironment proposed in the present invention.

By referring to FIGS. 1-8, a method for monitoring a forestry microenvironment comprises the following steps:

S1: moving a forestry detection vehicle to a monitoring position, starting a sampling device installed on the forestry detection vehicle, and drilling a sampling end into soil by the sampling device;

S2: inserting the sampling device on the forestry detection vehicle into the soil at a corresponding depth;

S3: disconnecting the sampled soil, and withdrawing the sampling device from the forestry detection vehicle to complete the sampling process;

S4: weighing the above soil sample quantitatively, placing the soil sample in a conical detection bottle, adding a quantitative solvent to the conical detection bottle, dissolving and filtering to obtain a standard solution for soil detection, and detecting the soil standard solution through a detection instrument.

The sampling device in S1 comprises a rack 1; the rack 1 is arranged as a portal frame; an outer sleeve 2 is arranged in the rack 1; the upper end of the outer sleeve 2 is rotatably installed on the rack 1; the inner end in the outer sleeve 2 is provided with an inner disc 3; the inner disc 3 is rotatably installed at the inner side of the outer sleeve 2; the inner disc 3 is fixedly provided with a connecting frame 4; the end of the connecting frame 4 is fixedly connected to the rack 1; a sampling mechanism is arranged in the outer sleeve 2; and the lower end of the sampling mechanism extends outside the outer sleeve 2 and is connected with the inner disc 3.

The sampling mechanism further comprises an inner cylinder 5; the upper end of the inner cylinder 5 extends into the outer sleeve 2; the inner cylinder 5 is provided with a plurality of upper and lower equidistant perforations 6; the perforations 6 penetrate through the inner cylinder 5 and the plurality of perforations 6 located at the same height are distributed in a circular array; storage grooves 7 are arranged at bottoms in the perforations 6; the bottom of the inner cylinder 5 is fixedly provided with a drill bit 8; the inner side of the outer sleeve 2 is provided with a plurality of spline grooves 9 distributed in a circular array; the outer side of the inner cylinder 5 is fixedly provided with a plurality of splines 10 distributed in a circular array; the splines 10 are matched with splines of the spline grooves 9; the upper end in the inner cylinder 5 is rotatably provided with a connecting piece 11; the sampling mechanism further comprises a screw rod 12; the screw rod 12 is arranged in the inner cylinder 5; the upper end of the screw rod 12 is rotatably installed at the bottom of the inner disc 3; the lower end of the screw rod 12 penetrates through the connecting piece 11 and is in threaded connection with the connecting piece 11; the top of the inner disc 3 is rotatably provided with a connecting shaft 14; the connecting shaft 14 penetrates through the inner disc 3 and is fixedly connected with the screw rod 12; the top of the outer sleeve 2 is fixedly provided with a connecting ring 15; the connecting ring 15 is sleeved and fixedly provided with a tooth ring 16; sealing plugs 17 are arranged in the storage grooves 7; the sealing plugs 17 are in interfere fit with the storage grooves 7; the sampling mechanism further comprises a plurality of connecting ropes 18; the connecting ropes 18 penetrate through the inner cylinder 5 and the storage grooves 7 and are fixedly connected with a plurality of sealing plugs 17 in the same column; the upper ends of the connecting ropes 18 are fixedly connected to the bottom of the inner disc 3; the sampling mechanism further comprises a driving assembly; and the driving assembly is installed on the rack 1 and connected with the connecting shaft 14.

Working principle: the driving assembly drives the connecting shaft 14 to rotate, and also drives the tooth ring 16 to rotate; the connecting shaft 14 rotates synchronously with the screw rod 12; and the screw rod 12 rotates and drives the inner cylinder 5 to move downward in a vertical direction. The tooth ring 16, the connecting ring 15 and the outer sleeve 2 rotate synchronously, and the outer sleeve 2 makes the inner cylinder 5 rotate synchronously through the transmission action of the spline grooves 9 and the splines 10, so that the drill bit 8 at the lower end of the inner cylinder 5 drills downward. The inner cylinder 5 moves into the soil layer, and the inner cylinder 5 stops after moving to a certain fixed depth. At this time, the connecting ropes 18 are in a stretched state and the connecting ropes 18 pull a plurality of sealing plugs 17. By driving the sealing plugs 17 away from the upper ports of the storage grooves 7, the storage grooves 7 are in an open state. At this time, the soil at different depths can enter the storage grooves 7 of different heights respectively, and then the inner cylinder 5 is taken out. Thus, the device can take out soil samples at different depths through single sampling, which can effectively improve the sampling efficiency and alleviate the labor burden of the monitoring work of the forestry microenvironment.

Embodiment 2

By referring to FIGS. 1-8, as another preferred embodiment of the present invention, the differences from embodiment 1 are that: the bottom of the screw rod 12 is fixedly provided with a stopper 13; the stopper 13 is arranged for limiting the screw rod 12; the surface of the screw rod 12 is sprayed with an anti-rust coating so that the screw rod 12 is not easy to be corroded; the present embodiment further comprises scale lines arranged at the outer side of the inner cylinder 5; and the depth at which the inner cylinder 5 is drilled into the soil layer is known by observing the scale lines on the inner cylinder 5.

The device needs to be fixed during operation. The fixing modes in the prior art are mainly realized by manual fixing devices. On the one hand, the physical strength of the personnel is consumed and the device is not fixed stably enough. On the other hand, because the shock generated by the motor on the device during operation is transmitted to the personnel, the personnel have the discomfort of numbness in the hands. Both ends of the bottom of the rack 1 are fixedly provided with embedded parts 19; the tops of the embedded parts 19 are provided with installing grooves 20; the installing grooves 20 are arranged in U shape; both ends of the embedded parts 19 are provided with guide ports 21; the guide ports 21 penetrate through the embedded parts 19 and are communicated with the installing grooves 20; and the bottoms of the embedded parts 19 are arranged in a triangular cone. The device is fixed to the ground surface by burying the embedded parts 19 at both ends into the soil layer. Two symmetrically distributed limiting parts 22 are arranged in the installing grooves 20; one end of the limiting parts 22 is sharpened; one end of the limiting parts 22 can penetrate through the guide ports 21; the upper sides of the limiting parts 22 are provided with guide plates 23; the guide plates 23 are located in the installing grooves 20 and fixedly connected to the embedded parts 19; the sampling mechanism further comprises a linkage mechanism; and the linkage mechanism is installed on the rack 1 and connected with a plurality of limiting parts 22. The linkage mechanism comprises two groups of linkage assemblies in mirror distribution; the linkage assemblies comprise two spaced transverse shafts 24; the transverse shafts 24 are rotatably installed in the installing grooves 20 respectively; the transverse shafts 24 are fixedly provided with two spaced friction wheels 25; the limiting parts 22 are fixedly provided with two spaced friction strips 26; the friction strips 26 are in transmission with the friction wheels 25 by friction force; worm wheels 27 are fixedly installed on the two transverse shafts 24; the tops of the embedded parts 19 are fixedly provided with two spaced supporting seats 28; two symmetrically distributed worms 29 are rotatably installed between the two supporting seats 28; the opposite ends of the two worms 29 are fixedly connected; and the worms 29 are engaged with the worm wheels 27 on the same side. The driving assembly comprises a motor 30; the motor 30 is fixedly connected to the rack 1; the output shaft end of the motor 30 is fixedly provided with a first rotating shaft 31; the end of the first rotating shaft 31 is fixedly provided with a first bevel gear 32; the rack 1 is rotatably provided with a second rotating shaft 33; the lower end of the second rotating shaft 33 is fixedly provided with a second bevel gear 34; the second bevel gear 34 is engaged with the first bevel gear 32; a gear 35 is fixedly installed on the second rotating shaft 33; the gear 35 is engaged with the tooth ring 16; and the upper end of the second rotating shaft 33 and the upper end of the connecting shaft 14 are provided with a first belt mechanism 36. The motor 30 drives the first rotating shaft 31 to rotate; the first rotating shaft 31 drives the first bevel gear 32 to rotate; the first bevel gear 32 drives the second bevel gear 34 to rotate; the second bevel gear 34 rotates synchronously with the second rotating shaft 33; the gear 35 on the second rotating shaft 33 rotates and drives the tooth ring 16 to rotate; and the tooth ring 16, the connecting ring 15 and the outer sleeve 2 rotate synchronously. At the same time, the first belt mechanism 36 is driven to the connecting shaft 14, and the connecting shaft 14 rotates synchronously with the screw rod 12, thereby providing drilling power for the drill bit 8.

Both ends of the top of the rack 1 are fixedly provided with grips 37, the grips 37 are sleeved with non-slip rubber sleeves, and the corners of the rack 1 are rounded. The device is conveniently carried by arranging the grips 37. The method further comprises a second belt mechanism 38 and a third belt mechanism 39; one end of the second belt mechanism 38 and one end of the third belt mechanism 39 are installed on the first rotating shaft 31; and the other end of the second belt mechanism 38 and the other end of the third belt mechanism 39 are installed on the worms 29 on both sides respectively.

Working principle: the motor 30 drives the first rotating shaft 31 to rotate; the first rotating shaft 31 drives the first bevel gear 32 to rotate; the first bevel gear 32 drives the second bevel gear 34 to rotate; the second bevel gear 34 rotates synchronously with the second rotating shaft 33; the gear 35 on the second rotating shaft 33 rotates and drives the tooth ring 16 to rotate; and the tooth ring 16, the connecting ring 15 and the outer sleeve 2 rotate synchronously. At the same time, the first belt mechanism 36 is driven to the connecting shaft 14, and the connecting shaft 14 rotates synchronously with the screw rod 12, thereby providing drilling power for the drill bit 8. The first rotating shaft 31 rotates and drives the worms 29 at both ends to rotate through the second belt mechanism 38 and the third belt mechanism 39. The worms 29 rotate and drive the worm wheels 27 to rotate. Because the rotating directions of the two connected worms 29 are opposite, the worm wheels 27 at both ends have opposite rotating directions. The worm wheels 27 rotate synchronously with the transverse shafts 24; the friction wheels 25 on the transverse shafts 24 rotate and drive the friction strips 26 to move; the friction strips 26 move synchronously with the limiting parts 22; and the limiting parts 22 at both sides are inserted into the soil layer synchronously. The device is fixed by inserting the limiting parts 22 into the soil layer, which can further improve the stability of the device during operation. Compared with the existing manual fixing mode, the present invention saves the physical strength of the personnel and fixes the device more firmly. At the same time, the personnel are not in direct contact with the device, thereby avoiding the discomfort of the personnel.

What is claimed is:

1. A method for monitoring a forestry microenvironment, comprising the following steps:
    S1: moving a forestry detection vehicle to a monitoring position, starting a sampling device installed on the forestry detection vehicle, and drilling a sampling end into soil by the sampling device;
    S2: inserting the sampling device on the forestry detection vehicle into the soil at a corresponding depth;
    S3: disconnecting the sampled soil, and withdrawing the sampling device from the forestry detection vehicle to complete the sampling process;
    S4: weighing the above soil sample quantitatively, preparing the soil sample into a standard solution for soil detection, and detecting the standard solution for soil detection;
    the sampling device in S1 comprises a rack (1); the rack (1) is arranged as a portal frame; an outer sleeve (2) is arranged in the rack (1); an upper end of the outer sleeve (2) is rotatably installed on the rack (1); an inner end in the outer sleeve (2) is provided with an inner disc (3); the inner disc (3) is rotatably installed at an inner side of the outer sleeve (2);
    the inner disc (3) is fixedly provided with a connecting frame (4); an end of the connecting frame (4) is fixedly connected to the rack (1); a sampling mechanism is arranged in the outer sleeve (2); and a lower end of the sampling mechanism extends outside the outer sleeve (2) and is connected with the inner disc (3);
    the sampling mechanism further comprises an inner cylinder (5); an upper end of the inner cylinder (5) extends into the outer sleeve (2); the inner cylinder (5) is provided with a plurality of upper and lower equidistant perforations (6); the perforations (6) penetrate through the inner cylinder (5) and the plurality of perforations (6) located at the same height are distributed in a circular array; storage grooves (7) are arranged at bottoms in the perforations (6); a bottom of the inner cylinder (5) is fixedly provided with a drill bit (8); the inner side of the outer sleeve (2) is provided with a plurality of spline grooves (9) distributed in a circular array; an outer side of the inner cylinder (5) is fixedly provided with a plurality of splines (10) distributed in a circular array; the splines (10) are matched with splines of the spline grooves (9); the upper end in the inner cylinder (5) is rotatably provided with a connecting piece (11); the sampling mechanism further comprises a screw rod (12); the screw rod (12) is arranged in the inner cylinder (5); an upper end of the screw rod (12) is rotatably installed a bottom of the inner disc (3); a lower end of the screw rod (12) penetrates through the connecting piece (11) and is in threaded connection with the connecting piece (11); the top of the inner disc (3) is rotatably provided with a connecting shaft (14); the connecting shaft (14) penetrates through the inner disc (3) and is fixedly connected with the screw rod (12); a top of the outer sleeve (2) is fixedly provided with a connecting ring (15); the connecting ring (15) is sleeved and fixedly provided with a tooth ring (16);

sealing plugs (17) are arranged in the storage grooves (7); the sealing plugs (17) are in interference fit with the storage grooves (7); the sampling mechanism further comprises a plurality of connecting ropes (18); the connecting ropes (18) penetrate through the inner cylinder (5) and the storage grooves (7) and are fixedly connected with a plurality of the sealing plugs (17) one of a plurality of columns ; the-upper ends of the connecting ropes (18) are fixedly connected to the bottom of the inner disc (3); the sampling mechanism further comprises a driving assembly; and the driving assembly is installed on the rack (1) and connected with the connecting shaft (14).

2. The method for monitoring the forestry microenvironment according to claim 1, wherein a bottom of the screw rod (12) is fixedly provided with a stopper (13), and a surface of the screw rod (12) is sprayed with an anti-rust coating.

3. The method for monitoring the forestry microenvironment according to claim 1, further comprising scale lines arranged at the outer side of the inner cylinder (5).

4. The method for monitoring the forestry microenvironment according to claim 1, wherein both ends of the bottom of the rack (1) are fixedly provided with embedded parts (19); the tops of the embedded parts (19) are provided with installing grooves (20); the installing grooves (20) are arranged in U shape; both ends of the embedded parts (19) are provided with guide ports (21); the guide ports (21) penetrate through the embedded parts (19) and are communicated with the installing grooves (20); and bottoms of the embedded parts (19) are arranged in a triangular cone; one limiting part is arranged in the inner installing groove(20); the one end of the limiting part (22) is sharpened;

another end of the limiting part (22) can penetrate through the guide ports (21); the upper sides of the limiting part (22) are provided with guide plates (23); the guide plates (23) are located in the installing grooves (20) and fixedly connected to the embedded parts (19); the sampling mechanism further comprises a linkage mechanism; and the linkage mechanism is installed on the rack (1) and connected with a plurality of the limiting parts (22);

the linkage mechanism comprises two groups of linkage assemblies in mirror distribution; the linkage assemblies comprise two spaced transverse shafts (24); the transverse shafts (24) are rotatably installed in the installing grooves (20) respectively; the transverse shafts (24) are fixedly provided with two spaced friction wheels (25); the limiting parts (22) are fixedly provided with two spaced friction strips (26); the friction strips (26) are in connection with the friction wheels (25) by friction force; worm wheels (27) are fixedly installed on the two transverse shafts (24); the tops of the embedded parts (19) are fixedly provided with two spaced supporting seats (28); and two symmetrically distributed worms (29) are rotatably installed between the two supporting seats (28).

5. The method for monitoring the forestry microenvironment according to claim 4, wherein opposite ends of the two worms (29) are fixedly connected, and the worms (29) are engaged with the worm wheels (27) on the same side.

6. The method for monitoring the forestry microenvironment according to claim 1, wherein the driving assembly comprises a motor (30); the motor (30) is fixedly connected to the rack (1); and an output shaft end of the motor (30) is fixedly provided with a first rotating shaft (31).

7. The method for monitoring the forestry microenvironment according to claim 6, wherein an end of the first rotating shaft (31) is fixedly provided with a first bevel gear (32); the rack (1) is rotatably provided with a second rotating shaft (33); a lower end of the second rotating shaft (33) is fixedly provided with a second bevel gear (34); the second bevel gear (34) is engaged with the first bevel gear (32); a gear (35) is fixedly installed on the second rotating shaft (33); the gear (35) is engaged with the tooth ring (16); and an upper end of the second rotating shaft (33) and an upper end of the connecting shaft (14) are provided with a first belt mechanism (36).

8. The method for monitoring the forestry microenvironment according to claim 1, wherein both ends of the top of the rack (1) are fixedly provided with grips (37), the grips (37) are sleeved with non-slip rubber sleeves, and corners of the rack (1) are rounded.

9. The method for monitoring the forestry microenvironment according to claim 7, further comprising a second belt mechanism (38) and a third belt mechanism (39); one end of the second belt mechanism (38) and one end of the third belt mechanism (39) are installed on the first rotating shaft (31); and an other end of the second belt mechanism (38) and an other end of the third belt mechanism (39) are installed on the worms (29) on both sides respectively.

* * * * *